(12) United States Patent
Otsubo et al.

(10) Patent No.: US 8,236,732 B2
(45) Date of Patent: Aug. 7, 2012

(54) HERBICIDAL COMPOSITION

(75) Inventors: Toshiro Otsubo, Sanda (JP); Atsushi Watanabe, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1292 days.

(21) Appl. No.: 11/058,281

(22) Filed: Feb. 16, 2005

(65) Prior Publication Data
US 2006/0183641 A1 Aug. 17, 2006

(51) Int. Cl.
*A01N 25/00* (2006.01)
*A01N 29/00* (2006.01)
*A01N 31/00* (2006.01)
*A01N 33/24* (2006.01)

(52) U.S. Cl. ........ 504/343; 504/348; 504/349; 504/353; 504/356; 504/358

(58) Field of Classification Search .................. None
See application file for complete search history.

(56) References Cited

U.S. PATENT DOCUMENTS

| | | | |
|---|---|---|---|
| 4,626,276 A | 12/1986 | Luo | |
| 4,668,693 A * | 5/1987 | Tomioka et al. | 514/399 |
| 4,741,768 A | 5/1988 | Frazier et al. | |
| 5,084,087 A | 1/1992 | Hazen et al. | |
| 5,128,329 A * | 7/1992 | Minagawa et al. | 514/89 |
| 5,495,033 A | 2/1996 | Basu et al. | |
| 5,554,576 A | 9/1996 | Mookerjee et al. | |
| 5,624,883 A | 4/1997 | Basu et al. | |
| 6,177,396 B1 * | 1/2001 | Clapperton et al. | 510/405 |
| 6,296,864 B1 * | 10/2001 | Zen | 424/405 |
| 6,635,663 B1 * | 10/2003 | Zen | 514/345 |
| 6,683,030 B2 * | 1/2004 | Kober et al. | 504/313 |
| 2003/0040436 A1 * | 2/2003 | Emerson et al. | 504/150 |
| 2003/0104947 A1 | 6/2003 | Woznica et al. | |
| 2003/0125211 A1 | 7/2003 | Woznica et al. | |

FOREIGN PATENT DOCUMENTS

| WO | WO 01/67860 | * | 9/2001 |
|---|---|---|---|
| WO | WO 2004/017734 | * | 3/2004 |

* cited by examiner

*Primary Examiner* — Johann Richter
*Assistant Examiner* — Frank Choi
(74) *Attorney, Agent, or Firm* — Sughrue Mion, PLLC

(57) ABSTRACT

A herbicidal composition comprising i) clethodim, ii) a sulfonate surfactant such as calcium dodecylbenzenesulfonate, iii) a polyoxyalkylene polyaryl ether such as polyoxyethylene polyoxypropylene tristyryl phenyl ether and polyoxyalkylene distyryl phenyl ether, iv) an aromatic hydrocarbon, and optionally, v) an ester of fatty acid such as methyl oleate methyl palmitate, methyl laurate, isopropyl myristate, isopropyl palmitate, octyl laurate, octyl palmitate and butyl stearate gives good stability of the emulsion after it is diluted with water.

10 Claims, No Drawings

HERBICIDAL COMPOSITION

FIELD OF THE INVENTION

The present invention relates to a herbicidal composition.

BACKGROUND ARTS

Some compositions containing a herbicidal cyclohexanedione compound are known in U.S. Pat. No. 4,626,276, U.S. Pat. No. 4,741,768, U.S. Pat. No. 5,084,087 and U.S. Pat. No. 5,554,576.

SUMMARY OF THE INVENTION

The present invention provides a herbicidal composition comprising i) clethodim, ii) a sulfonate surfactant, iii) a polyoxyalkylene polyaryl ether and iv) an aromatic hydrocarbon.

According to the present invention, the composition containing clethodim can provide a stable emulsion when it is diluted with hard water as well as normal water.

DETAILED DESCRIPTION OF THE INVENTION

In the present invention, clethodim is an herbicidal ingredient, and the chemical name of clethodim is (±)-2-[(E)-1-[(E)-3-chloroallyloxyimino]propyl]-5-[2-(ethylthio)propyl]-3-hydroxyclohex-2-enone of the formula:

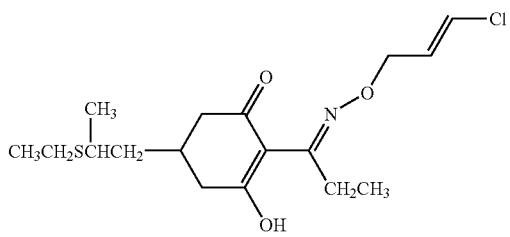

It can be obtained in the market, for example, it is provided by Valent U.S.A. Corporation, Tomen Agro, Inc. or Arvesta Corporation.

The content of clethodim in the herbicidal composition of the present invention is generally 5% to 40% by weight, preferably 10% to 30% by weight.

The sulfonate surfactant means an anionic surfactant having at least one sulfonic acid salt group in the molecule. Examples of the sulfonate surfactant include salts of alkylbenzene sulfonic acid (e.g., (C8-C15 alkyl)benzenesulfonate), salts of alkylnaphthalene sulfonic acid, salts of alkylsulfonic acid, salts of alkyl ether sulfonic acid, salts of fatty alcohol ether sulfonic acid and salts of polyoxyalkylene tristyrylphenyl ether sulfonic acid. Typical examples of the salt are calcium, sodium and potassium salts. Typical examples of the sulfonate are dodecylbenzenesulfonate, diisopropylnaphthalenesulfonate, diisobutylnaphthalenesulfonate, α-olefinsulfonate and dialkylsulfosuccinate. Among them, calcium dodecylbenzenesulfonate, sodium dodecylbenzenesulfonate and potassium dodecylbenzenesulfonate are preferably used.

The content of the sulfonate surfactant in the herbicidal composition of the present invention is generally 0.1% to 10% by weight, preferably 0.1% to 5% by weight.

The polyoxyalkylene polyaryl ether means a nonionic surfactant having two or more aromatic ring, wherein at least one aromatic ring has a polyoxyalkylene group, and an ether structure in the molecule. Typical examples of the polyoxyalkylene polyaryl ether include polyoxyalkylene styryl phenyl ether, polyoxyalkylene styryl phenylphenyl ether, polyoxyalkylene benzyl phenyl ether, polyoxyalkylene benzyl phenylphenyl ether and polyoxyalkylene bisphenyl ether. The polyoxyalkylene part is generally polyoxyethylene, polyoxypropylene or block copolymer of polyoxyethlene and polyoxypropylene. Typical examples are polyoxyalkylene tristyryl phenyl ether (e.g., polyoxyethylene tristyryl phenyl ether, polyoxyethylene polyoxypropylene tristyryl phenyl ether) and polyoxyalkylene distyryl phenyl ether (e.g., polyoxyethylene distyryl phenyl ether).

The HLB of the polyoxyalkylene polyaryl ether is preferably 12 to 15. HLB means Hydrophilic-Lipophilic Balance which is well known in the field of surfactant.

The content of the polyoxyalkylene polyaryl ether in the herbicidal composition of the present invention is generally 0.1% to 30% by weight, preferably 0.1% to 20% by weight.

The aromatic hydrocarbon is generally a solvent that can dissolve clethodim. Namely, the aromatic hydrocarbon is usually used in the amount that can dissolve the clethodim contained in the herbicidal composition.

Examples of the aromatic hydrocarbon include xylene, phenylxylylethane, Hisol SAS-296 (a mixture of 1-phenyl-1-xylylethane and 1-phenyl-1-ethylphenylethane, commercial name of Nippon Petroleum Company), Cactus Solvent HP-DMN (containing 80% of dimethylnaphthalene, commercial name of Nikko Petrochemical Company), Cactus Solvent P-100 (alkylbenzene having 9 to 10 of carbon number, commercial name of Nikko Petrochemical Company), Aromatic 150 (aromatic hydrocarbon, commercial name of ExxonMobil Chemical) and Aromatic 200 (aromatic hydrocarbon, commercial name of ExxonMobil Chemical).

The content of the aromatic hydrocarbon in the herbicidal composition of the present invention is generally 10% to 89.8% by weight.

Further, the herbicidal composition optionally comprises the other solvent, auxiliaries such as esters of fatty acid, antioxidant, fungicide, perfume, dyestuff, and so on.

The esters of fatty acid are generally can work as enhancer of bioefficacy. The formula of esters of fatty acid is RCOOR'; wherein R is an alkyl group having 7 to 21 carbon atoms or an alkenyl group having 7 to 21 carbon atoms, and R' is an alkyl group having 1 to 8 carbon atoms. Examples of the group given by the formula RCO include palmitoyl, myristoyl, stearoyl, lauroyl and oleoyl. Examples of R' are methyl, ethyl, isopropyl, butyl, isobutyl and octyl. Typical examples of the esters of fatty acid are methyl oleate, methyl palmitate, methyl laurate, isopropyl myristate, isopropyl palmitate, octyl laurate, octyl palmitate and butyl stearate.

When the ester of fatty acid is used, the content of the ester of fatty acid in the herbicidal composition is generally 0.1% to 79.8% by weight, preferably 10% to 50% by weight. In addition, when the ester of fatty acid is used, the content of the aromatic hydrocarbon in the herbicidal composition of the present invention is preferably 10% to 60% by weight.

Preferably, propyl gallate is used for antioxidant; the content of the propyl gallate in the herbicidal composition is generally 0.01% to 10% by weight, preferably 0.1% to 3% by weight.

The herbicidal composition of the present invention can be prepared by mixing i) clethodim, ii) a sulfonate surfactant, iii) a polyoxyalkylene polyaryl ether and iv) an aromatic hydrocarbon, and optionally the other solvent, auxiliaries and so on.

The herbicidal composition of the present invention is utilized as an emulsifiable concentrate in general, namely it is diluted with water to give an emulsion and applied to weeds, especially graminaceous weeds such as *Agropyron tsukushiense*, barnyardgrass (*Echinochloa crus-galli*), green foxtail (*Setaria viridis*), giant foxtail (*Setaria faberi*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*) and bermudagrass (*Cynodon dactylon*) in broad-leaf crop (e.g. soybean, cotton, sugarbeet, peanut) fields. The application dosage is generally 10 g to 1000 g per hectare in the amount of clethodim, although it may vary with the kinds of objective weeds, weather conditions and so on. The dilution of the herbicidal composition can also be used for aerial application by helicopter, plane or radio-controlled helicopter. The herbicidal composition of the present invention may be diluted with water containing a spreading agent. Examples of the spreading agent include Agridex (commercial name of Helena Chemical Corporation), Dynamic (commercial name of Helena Chemical Corporation), Induce (commercial name of Helena Chemical Corporation) and Silwet L-77 (manufactured by Nihon Unicar).

Example 1

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene polyoxypropylene tristyryl phenyl ether (HLB 13.5, SOPROPHOR 796P supplied by Rhodia) | 1.00 wt % |
| Methyl oleate (AGNIQUE ME 181-U supplied by Cognis) | 40.00 wt % |
| Aromatic 150 (aromatic hydrocarbon, commercial name of ExxonMobil Chemical) | 43.83 wt % |

Example 2

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 3.34 wt % |
| Polyoxyethylene polyoxypropylene tristyryl phenyl ether (HLB 13.5, SOPROPHOR 796P supplied by Rhodia) | 2.00 wt % |
| Methyl oleate (AGNIQUE ME 181-U supplied by Cognis) | 40.00 wt % |
| Aromatic 150 (aromatic hydrocarbon, commercial name of ExxonMobil Chemical) | 41.16 wt % |

Example 3

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 3.34 wt % |
| Polyoxyethylene polyoxypropylene tristyryl phenyl ether (HLB 13.5, SOPROPHOR 796P supplied by Rhodia) | 2.00 wt % |
| Isopropyl myristate (Kessco IPM supplied by Stepan) | 40.00 wt % |
| Aromatic 150 (aromatic hydrocarbon, commercial name of ExxonMobil Chemical) | 41.16 wt % |

Example 4

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene tristyryl phenyl ether (HLB 12.5, SOPROPHOR BSU supplied by Rhodia) | 9.00 wt % |
| Methyl oleate (AGNIQUE ME 181-U supplied by Cognis) | 40.00 wt % |
| Aromatic 150 (aromatic hydrocarbon, commercial name of ExxonMobil Chemical) | 35.83 wt % |

Example 5

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene polyoxypropylene tristyryl phenyl ether (HLB 13.5, SOPROPHOR 796P supplied by Rhodia) | 9.00 wt % |
| Methyl oleate (AGNIQUE ME 181-U supplied by Cognis) | 40.00 wt % |
| Aromatic 150 (aromatic hydrocarbon, commercial name of ExxonMobil Chemical) | 35.83 wt % |

Example 6

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene tristyryl phenyl ether (HLB 14.5, SOPROPHOR S25 supplied | 9.00 wt % |

-continued

| | |
|---|---|
| by Rhodia) | |
| Methyl oleate (AGNIQUE ME 181-U supplied by Cognis) | 40.00 wt % |
| Aromatic 150 (aromatic hydrocarbon, commercial name of ExxonMobil Chemical) | 35.83 wt % |

Example 7

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene tristyryl phenyl ether (HLB 12.5, SOPROPHOR BSU supplied by Rhodia) | 9.00 wt % |
| Aromatic 150 (aromatic hydrocarbon, commercial name of ExxonMobil Chemical) | 75.83 wt % |

Example 8

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene polyoxypropylene tristyryl phenyl ether (HLB 13.5, SOPROPHOR 796P supplied by Rhodia) | 9.00 wt % |
| Aromatic 150 (aromatic hydrocarbon, commercial name of ExxonMobil Chemical) | 75.83 wt % |

Example 9

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 3.34 wt % |
| Polyoxyethylene tristyryl phenyl ether (HLB 14.5, SOPROPHOR S25 supplied by Rhodia) | 2.00 wt % |
| Aromatic 150 (aromatic hydrocarbon, commercial name of ExxonMobil Chemical) | 81.16 wt % |

Test Example 1

342 ppm hard water (obtained by dissolving 3.04 g of anhydrous calcium chloride and 0.139 g of magnesium chloride hexahydrate in distilled water and making up to 1 liter) was charged in a 95 ml-cylinder with lid, and keep at room temperature. Then, 5 ml of each of the compositions obtained in Examples 1 to 10 was added. The cylinders were inverted 10 times in 20 seconds. After keeping the cylinders for two hours at room temperature, the separation of the top layer was observed as emulsion stability.

| Example No. | Emulsion stability |
|---|---|
| 1 | excellent |
| 2 | excellent |
| 3 | excellent |
| 4 | good |
| 5 | acceptable |
| 6 | acceptable |
| 7 | good |
| 8 | good |
| 9 | acceptable |

Example 10

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene polyoxypropylene tristyryl phenyl ether (HLB 13.5, SOPROPHOR 796P supplied by Rhodia) | 1.00 wt % |
| Isopropyl myristate (Kessco IPM supplied by Stepan) | 40.00 wt % |
| Aromatic 150 (aromatic hydrocarbon, commercial name of ExxonMobil Chemical) | 43.83 wt % |

Example 11

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene polyoxypropylene tristyryl phenyl ether (HLB 13.5, SOPROPHOR 796P supplied by Rhodia) | 1.00 wt % |
| Octyl palmitate (Kessco Octyl Palmitate supplied by Stepan) | 40.00 wt % |
| Aromatic 150 (aromatic hydrocarbon, commercial name of ExxonMobil Chemical) | 43.83 wt % |

Example 12

The following ingredients were thoroughly mixed to give a herbicidal composition of the present invention.

| | |
|---|---|
| Clethodim (purity: 93%) | 13.50 wt % |
| Calcium dodecylbenzenesulfonate (60% calcium dodecylbenzenesulfonate in 2-ethylhexanol, AGNIQUE ABS 60C supplied by Cognis) | 1.67 wt % |
| Polyoxyethylene polyoxypropylene tristyryl phenyl ether (HLB 13.5, SOPROPHOR 796P supplied by Rhodia) | 1.00 wt % |
| Butyl Stearate (Kessco BS COS supplied by Stepan) | 40.00 wt % |
| Aromatic 150 (aromatic hydrocarbon, commercial name of ExxonMobil Chemical) | 43.83 wt % |

Test Example 2

Each of the tested compositions was diluted with water and applied to weeds (post-emergency test). The weed sizes are as follows: Barnyardgrass (6 inches), Seedling Johnsongrass (4-6 inches), Broadleaf Signalgrass (3-4 inches) and Giant Foxtail (4-5 inches). The application rate was 34 g per hectare in the amount of clethodim and the splayed volume was 188 litters per hectare. After 3 days, the second application was conducted. Observation was conducted after 21 days after first application. Evaluation of weed control was used 0-10 scale. (0: no damage, 10: complete kill, 8, 9 and 10 are usually practically acceptable and less than 6 is sufficient.) The evaluation number of weed control described below is the average over 4 weeds: Barnyardgrass, Seedling Johnsongrass, Broadleaf Signalgrass and Giant Foxtail.

| Example No. | Weed control |
|---|---|
| 1 | 8 |
| 10 | 9 |
| 11 | 9 |
| 12 | 9 |
| No application | 0 |

We claim:

1. A herbicidal composition which comprises clethodim, a sulfonate surfactant, polyoxyalkylene tristyryl phenyl ether and/or polyoxyalkylene distyryl phenyl ether, an aromatic hydrocarbon, and propyl gallate.

2. The herbicidal composition according to claim 1, which comprises 5% to 40% by weight of clethodim, 0.1% to 10% by weight of a sulfonate surfactant, 0.1% to 30% by weight of polyoxyalkylene tristyryl phenyl ether and/or polyoxyalkylene distyryl phenyl ether, 10% to 89.8% by weight of an aromatic hydrocarbon, and propyl gallate.

3. The herbicidal composition according to claim 1, which comprises 10% to 30% by weight of clethodim, 0.1% to 5% by weight of a sulfonate surfactant, 0.1% to 20% by weight of polyoxyalkylene tristyryl phenyl ether and/or polyoxyalkylene distyryl phenyl ether, 10% to 89.8% by weight of an aromatic hydrocarbon, and propyl gallate.

4. A herbicidal composition according to claim 1, wherein the composition further comprises an ester of fatty acid.

5. The herbicidal composition according to claim 4, which comprises 5% to 40% by weight of clethodim, 0.1% to 10% by weight of a sulfonate surfactant, 0.1% to 30% by weight of polyoxyalkylene tristyryl phenyl ether and/or polyoxyalkylene distyryl phenyl ether, 10% to 89.8% by weight of an aromatic hydrocarbon, propyl gallate and 0.1% to 79.8% of an ester of fatty acid.

6. The herbicidal composition according to claim 4, which comprises 10% to 30% by weight of clethodim, 0.1% to 5% by weight of a sulfonate surfactant, 0.1% to 20% by weight of polyoxyalkylene tristyryl phenyl ether and/or polyoxyalkylene distyryl phenyl ether, 10% to 60% by weight of an aromatic hydrocarbon, propyl gallate and 10% to 50% of an ester of fatty acid.

7. The herbicidal composition according to claim 6, wherein the ester of fatty acid is methyl oleate.

8. The herbicidal composition according to any of claims 1-7, wherein the HLB of the polyoxyalkylene tristyryl phenyl ether and/or polyoxyalkylene distyryl phenyl ether is from 12 to 15.

9. The herbicidal composition according to claim 8, wherein the polyoxyalkylene tristyryl phenyl ether and/or polyoxyalkylene distyryl phenyl ether is polyoxyethylene polyoxypropylene tristyryl phenyl ether.

10. The herbicidal composition according to any of claims 1-7, wherein the sulfonate surfactant is a salt of dodecylbenzenesulfonic acid.

* * * * *